United States Patent
Chao et al.

(10) Patent No.: US 12,004,847 B2
(45) Date of Patent: Jun. 11, 2024

(54) RADIAL ARTERY SIGNAL MEASURING DEVICE

(71) Applicant: National Yang Ming Chiao Tung University, Hsinchu (TW)

(72) Inventors: Paul C.P. Chao, Taipei (TW); Chia-Hsiu Yeh, Taichung (TW)

(73) Assignee: NATIONAL YANG MING CHIAO TUNG UNIVERSITY, Hsinchu (TW)

( * ) Notice: Subject to any disclaimer, the term of this patent is extended or adjusted under 35 U.S.C. 154(b) by 288 days.

(21) Appl. No.: 17/342,675

(22) Filed: Jun. 9, 2021

(65) Prior Publication Data
US 2021/0386303 A1    Dec. 16, 2021

(30) Foreign Application Priority Data
Jun. 10, 2020    (TW) .................................. 109119567

(51) Int. Cl.
*A61B 5/026*    (2006.01)
*A61B 5/0295*    (2006.01)

(52) U.S. Cl.
CPC .......... *A61B 5/0261* (2013.01); *A61B 5/0295* (2013.01); *A61B 2562/0238* (2013.01); *A61B 2562/164* (2013.01)

(58) Field of Classification Search
CPC ...... A61B 2562/0238; A61B 2562/164; A61B 5/0261; A61B 5/0295
See application file for complete search history.

(56) References Cited

U.S. PATENT DOCUMENTS

2020/0129077 A1*  4/2020  Rogers ................. A61B 5/0261
2021/0161473 A1*  6/2021  Blomqvist ........... A61B 5/7214

* cited by examiner

*Primary Examiner* — Mark D Remaly
(74) *Attorney, Agent, or Firm* — RABIN & BERDO, P.C.

(57) ABSTRACT

A radial artery signal measuring device includes a flexible signal sensor, a signal processor, and a flexible cable. The flexible signal sensor is fixed on a skin surface over a radial artery by a patch during use. The flexible signal sensor includes a flexible substrate, at least one infrared light source, and a light detector. The at least one infrared light source is used to emit an infrared light to the radial artery, wherein the wavelength of the light source is infrared light greater than 1000 nm. The light detector is used to receive the infrared light reflected by the radial artery and generate a radial artery signal. The signal processor includes a housing for fitting the wrist of a user, a circuit board, a microprocessor, and a battery. The flexible cable is used to transmit the radial artery signal to the microprocessor.

5 Claims, 4 Drawing Sheets

RADIAL ARTERY SIGNAL MEASURING DEVICE

CROSS-REFERENCE TO RELATED APPLICATION

This application claims priority from Taiwan Application No. 109119567, filed on Jun. 10, 2020, in the Taiwan Intellectual Property Office, the content of which is hereby incorporated by reference in their entirety for all purposes.

BACKGROUND

1. Technical Field

The invention relates to a measuring device and particularly to a radial artery signal measuring device with a flexible sensor patch by using infrared light sources.

2. Description of the Related Art

In recent years, the lifestyle changes. Chronic diseases, such as heart disease, diabetes, stroke, and cancer, have replaced acute infectious diseases as modern civilization diseases and plague many people. In addition to harming personal health, chronic diseases can also impose a heavy burden on the family economy and national medical expenditures. Therefore, the prevention and treatment of chronic diseases has become an issue that countries all over the world must face. At present, hospitals have a variety of chronic disease detection methods, but many patients often detect chronic diseases before the time for early treatment. Therefore, if it can be implemented in any place and time and can be tested regularly, it can play the role of early detection and early treatment.

Therefore, at present, major technology factories in the world have launched portable or wearable personal health detection devices, and the health detection devices for detecting cardiovascular diseases occupy most of the market. According to statistics from the World Health Organization, coronary artery disease and stroke are the top ten causes of death in the world. In Taiwan, although cancer still occupies the top ten causes of death, heart diseases and cerebrovascular diseases occupy the second and third places. And among the top ten causes of death, half are related to cardiovascular disease, and the combined death percentage exceeds that of cancer, which shows the seriousness of this threat. Therefore, wearable detection devices for detecting cardiovascular diseases are flourishing.

Currently, the main technology used in wearable detection devices for detecting cardiovascular diseases is Photoplethysmography (PPG), which uses light sensing elements to illuminate the surface of the skin, and uses the principle that blood absorbs light energy to record the signals induced by changes in light. When the heart beats periodically, the blood volume also changes periodically. Therefore, the light received by the light sensing element will also induce a voltage and generate a signal along with the change of the blood volume. That is, the amplitude of the photoplethysmography (PPG) signal changes proportionally with the blood entering and leaving the tissue. The signal of photoplethysmography can be simply obtained. Compared with other instruments, photoplethysmography has the advantages of lighter equipment, simpler operation, non-invasiveness, high affinity and low cost, so many scholars have invested in research.

However, most of the known wearable devices that use photoplethysmography physiological sensors to detect cardiovascular diseases have problems of poor signal quality, insufficient flexibility in use, and poor patch fixation effects. The reason is that the sensor and housing used in wearable devices are fixed together. Therefore, when the human body is in motion, the movement of the housing will have a linkage relationship with the sensor, so that the relative displacement between the human body and the sensor will cause interference noise, causing motion artifact noise between the human body and the sensor. And sometimes when the patch is attached to the expected position of the artery, because the sensor is made of rigid material, the sensor structure cannot be changed with the structure of the human body. As a result, insufficient adhesion causes the sensor to detect environmental noise. It is also possible that the user does not know the correct position of the artery and sticks to other positions, causing the sensor to detect other signals.

SUMMARY

In order to solve the above problems, an aspect of the invention is to provide a radial artery signal measuring device, which includes a flexible signal sensor, a signal processor, and a flexible cable.

The flexible signal sensor is fixed on a skin surface on a radial artery by a patch during use. The flexible signal sensor comprises a flexible substrate, at least one infrared light source and a light detector. The at least one infrared light source is disposed on the flexible substrate and used to emit an infrared light to the radial artery, wherein the wavelength of the light source is infrared light greater than 1000 nm. The light detector is disposed on the flexible substrate and used to receive the infrared light reflected by the radial artery and generate a radial artery signal. The signal processor comprises a housing for fitting the wrist of a user, a circuit board, a microprocessor and a battery. The microprocessor is disposed on the circuit board and used to analyze the radial artery signal. The battery is disposed on the circuit board for providing power to the microprocessor. The flexible cable is used to transmit the radial artery signal to the microprocessor from the flexible signal sensor and transmit electrical energy to the flexible signal sensor from the battery.

In an embodiment of this invention, the at least one infrared light source is arranged to surround the light detector.

In an embodiment of this invention, the at least one infrared light source is an infrared light emitting diode, an infrared organic light emitting diode, or any combinations thereof.

In an embodiment of this invention, the light detector is an organic photodetector.

In an embodiment of this invention, the light detector is a quantum dot detector.

According to another aspect of the invention, a method of measuring a radial artery signal is provided. The method comprises: wearing the radial artery signal measuring device on the wrist of the user; fixing the flexible signal sensor on the skin surface over the radial artery by a patch; emitting the infrared light to the radial artery by the at least one infrared light source; receiving the infrared light reflected from the radial artery by the light detector to generate the radial artery signal; and analyzing the radial artery signal by the microprocessor.

In an embodiment of this invention, the radial artery signal is analyzed by photoplethysmography (PPG).

In an embodiment of this invention, the flexible signal sensor and the skin surface have no relative displacement when the signal processor moves.

Based on the above, the following advantages are provided.

(1) In some embodiments of this invention, the at least one infrared light source is used to provide infrared light having a deeper penetration depth more than red or green light traditionally used. Hence, the biological signal generated by the human radial artery can be more accurately measured.

(2) In some embodiments of this invention, a flexible substrate is used to make the sensing device, so that the sensing device can fit more closely on the user's skin surface to overcome motion artifacts generated by the human body motion state or noise interference generated by ambient light, and is more comfortable.

BRIEF DESCRIPTION OF THE DRAWINGS

The invention will become more apparent to those with ordinary skills in the art with reference to the following detailed description in conjunction with the accompanying drawings, among which.

DETAILED DESCRIPTION

In this disclosure, many specific details are provided so that the technical features, content and advantages of the embodiments of the invention can be thoroughly understood. The drawings used therein are only for illustration and auxiliary manual purposes, and may not be the true proportions and precise configurations after the implementation of the invention. Therefore, the scale and configuration relationship of the attached drawings should not limit the patent scope of the present invention in actual implementation.

Figure 1:
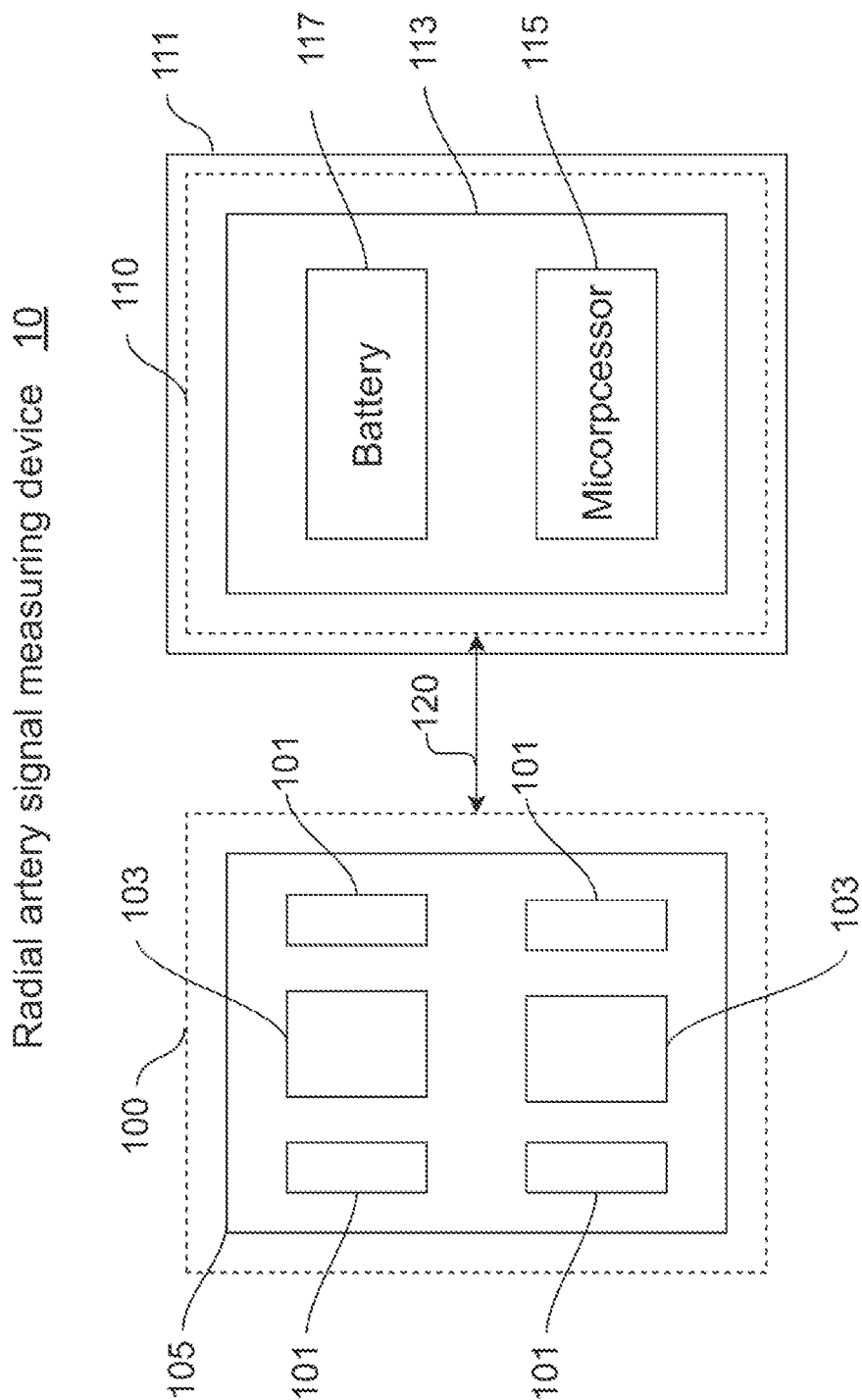
FIG. 1, which is a diagram of a radial artery signal measuring device according to an embodiment of the invention.

Please refer to FIG. 1, which is a diagram of a radial artery signal measuring device according to an embodiment of the invention. A radial artery signal measuring device 10 includes a flexible signal sensor 100, a signal processor 110 and a flexible cable 120. The signal processor 110 comprises a housing 111 for fitting a wrist of a user, a circuit board 113, a microprocessor 115, and a battery 117. The microprocessor 115 is disposed on the circuit board 113 and used to analyze the radial artery signal. The battery 117 is disposed on the circuit board 113 for providing power to the microprocessor 115. The flexible cable 120 is used to transmit the radial artery signal to the microprocessor 115 from the flexible signal sensor 100 and transmit electrical energy to the flexible signal sensor from the battery 117.

Figure 2:
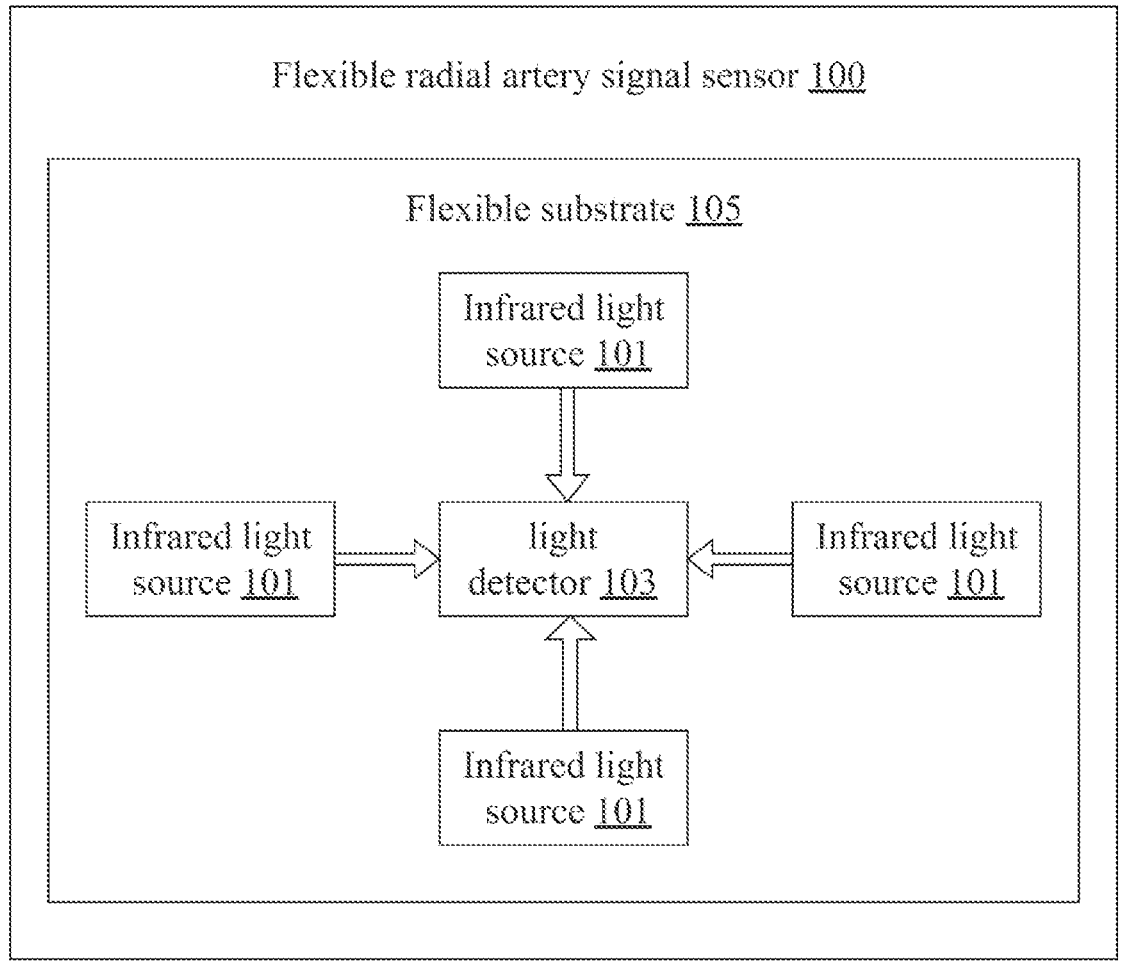
FIG. 2, which is a diagram of a flexible signal sensor according to an embodiment of the invention.

Please also refer to FIG. 2, which is a diagram of a flexible signal sensor according to an embodiment of the invention. The flexible signal sensor 100 is fixed on a skin surface over a radial artery by a patch during use. Hence, the flexible signal sensor 100 and the skin surface will have no relative displacements even though the signal processor 110 moves. The flexible signal sensor 100 comprises a flexible substrate 105, at least one infrared light source 101 and a light detector 103. The at least one infrared light source 101 is disposed on the flexible substrate 105 and used to emit an infrared light to the radial artery, wherein the wavelength of the infrared light is greater than 1000 nm. The light detector 103 is disposed on the flexible substrate 105 and used to receive the infrared light reflected by the radial artery and generate a radial artery signal.

Figure 3:
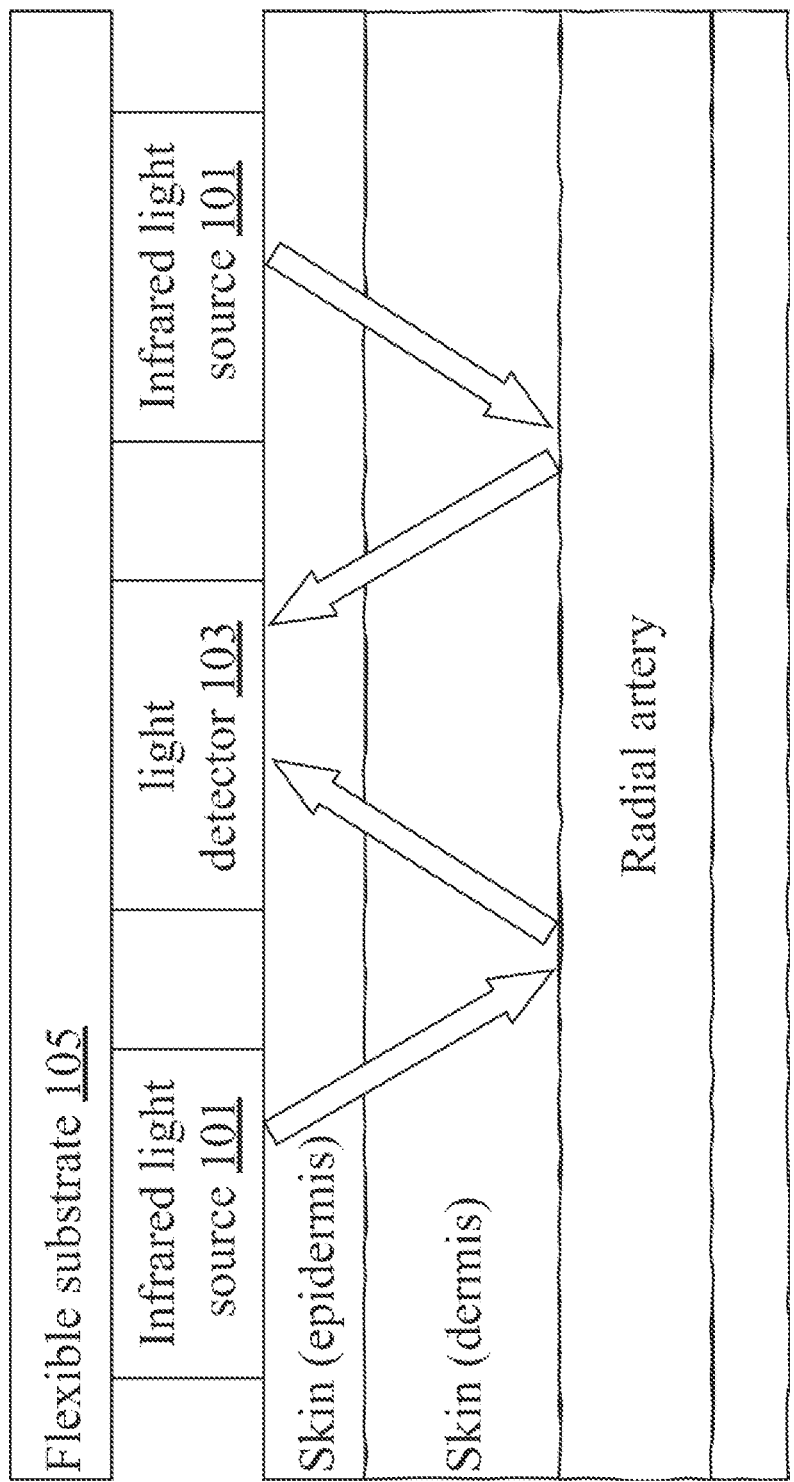
FIG. 3 is a cross section diagram of a flexible signal sensor according to an embodiment of the invention.

Please refer to FIG. 3, which is a cross sectional diagram of a flexible signal sensor on a skin surface over a radial artery of a user, according to an embodiment of the invention. When the flexible signal sensor 100 is used, it can use the characteristics of infrared light with a wavelength greater than 1000 nm to penetrate the skin to a certain depth and then be reflected. For example, when the flexible signal sensor 100 is fixed on the skin surface on a radial artery of a wrist, the incident IR light can penetrate to the depth of a radial artery and then be reflected by the radial artery. Therefore, the biological signals from the radial artery, such as blood pressure, blood flow, blood oxygen, etc., can be obtained by using the light detector 103 to receive the reflected signal from the radial artery.

In an embodiment of this invention, in order to further improve the detection stability and accuracy of the biological signals, the flexible signal sensor 100 can be fixed on the skin surface over a radial artery of a wrist, which can be used to avoid motional artifact noise. The motional artifact noise is a kind of noise interference generated in the state of human motion.

In an embodiment of this invention, in order to further improve the detection stability and accuracy of the biological signals, the relative positions of the at least one infrared light sources 101 and the light detector 103 can be further properly arranged. For example, the at least one infrared light sources 101 are arranged around the light detector 103 in a specific arrangement to reduce the motional artifacts generated by the human body in the state of motion or the noise interference generated by the ambient light and thus obtain more stable and accurate measurement results. However, the relative positions of the at least one infrared light sources 101 and the light detector 103 of the invention are not limited thereto.

In an embodiment of this invention, the at least one infrared light source 101 may be achieved by integrating a light-emitting diode (LED), an organic light-emitting diode (OLED), or a combination thereof on the flexible substrate 105.

In another embodiment of this invention, the light detector 103 can be achieved by integrating an organic photodetector, a quantum dot detector, or a combination thereof on the flexible substrate 105.

Figure 4:
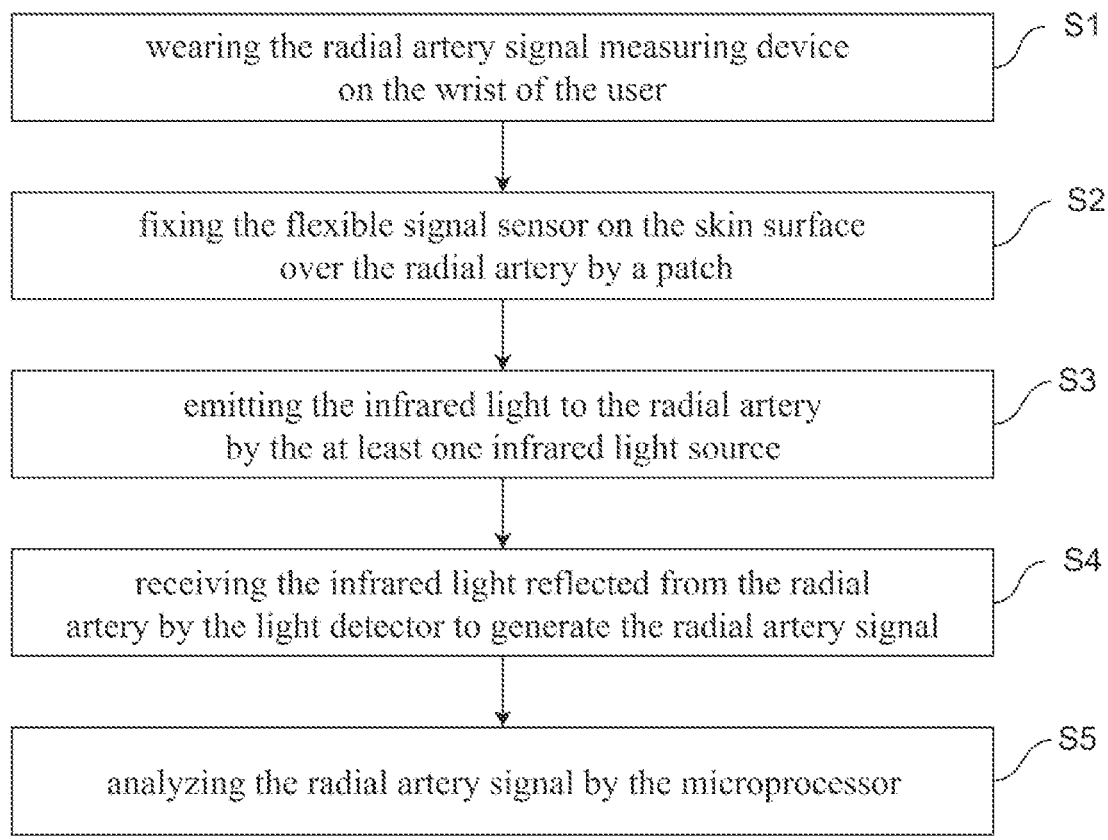
FIG. 4 is a diagram of a flowchart of a method of measuring a radial artery signal according to an embodiment of the invention.

Please refer to FIG. 4, which is a diagram of a flowchart of a method of measuring a radial artery signal according to an embodiment of the invention. A method of measuring a radial artery signal comprises the following steps (S1-S6).

In step S1: The radial artery signal measuring device 10 is worn on a wrist of a user. As stated above, the radial artery signal measuring device 10 comprises the flexible signal sensor 100 and the signal processor 110.

In step S2: The signal sensor on the skin surface over the radial artery is fixed by a patch. In more detail, the flexible signal sensor 100 is extended to a position of a skin surface over a radial artery from the housing 111 of the signal processor 110 by the flexible cable 120. The flexible signal sensor 100 is electrically connected to the signal processor 110.

In step S3: An infrared light is emitted to the radial artery by the at least one infrared light source 101 of the flexible signal sensor 100, and the wavelength of the infrared light is greater than 1000 nm.

In step S4: The infrared light reflected from the radial artery is received by the light detector 103 to generate a radial artery signal.

In step S5: The radial artery signal is analyzed by the microprocessor 115. In an embodiment of this invention, the radial artery signal may be analyzed by photoplethysmography (PPG).

The photoplethysmography (PPG) analysis can be achieved by an adaptive controller of a sensing system of the photoplethysmography. The amplitude of the driving signal (driving current or driving voltage) of the light source or/and the gain of the amplifier can be adaptively adjusted according to whether the PPG signal meets the requirements. The signal quality of the PPG signal obtained by the sensing system can be increased, and the accuracy, stability and sensitivity of the measurement can also be improved accordingly. In addition, the algorithm that adaptively adjusts the amplitude of the driving signal of the light source or/and the gain of the amplifier can be introduced into the algorithm of artificial intelligence to quickly make the PPG signal meet the demand. This algorithm can be implemented by the aforementioned microprocessor 115.

According to some embodiments of this invention, the flexible signal sensor 100 and the skin surface have no relative displacement when the signal processor 110 moves. That is, when the signal processor 110 is worn on the wrist or arm of a human body and moves on the wrist or arm of the hand, the flexible signal sensor 100 can be free from the influence of the signal processor 110 since the function of the patch and the flexible cable 120. The flexible signal sensor 100 maintains a relative position fixed on the skin surface over the radial artery to improve the detection stability and accuracy of biological signals.

However, the above are only preferred embodiments of the invention, and the scope of implementation of the invention cannot be limited thereto. That is, all equal changes and modifications made in accordance with the scope of the patent application of the invention should still fall within the scope of the patent scope of the invention.

What is claimed is:

1. A radial artery signal measuring device, comprising:
    a flexible signal sensor configured to be fixed on a first position of a skin surface over a radial artery of a wrist of a user by a patch during use, wherein the flexible signal sensor comprises:
        a flexible substrate;
        at least one infrared light source disposed on the flexible substrate and configured to emit an infrared light to the radial artery, wherein a wavelength of the infrared light is greater than 1000 nm; and
        a light detector disposed on the flexible substrate and configured to receive the infrared light reflected by the radial artery to generate a radial artery signal;
    a signal processor spatially separated from the flexible signal sensor to be movably disposed on a second position of the skin surface of the wrist of the user during use, wherein the signal processor comprises:
        a circuit board;
        a microprocessor disposed on the circuit board and configured to analyze the radial artery signal;
        a battery disposed on the circuit board for providing power to the microprocessor; and
        a housing for surrounding the circuit board, the microprocessor, and the battery, and for fitting the wrist of the user; and
    a flexible cable used to electrically connect the flexible signal sensor and the signal processor to transmit the radial artery signal to the microprocessor from the flexible signal sensor and transmit electrical energy to the flexible signal sensor from the battery, such that the flexible signal sensor has no displacement on the skin surface of the user when the signal processor moves on the wrist of the user.

2. The radial artery signal measuring device of claim 1, wherein the at least one infrared light source is arranged to surround the light detector.

3. The radial artery signal measuring device of claim 1, wherein the at least one infrared light source is an infrared light emitting diode, an infrared organic light emitting diode, or any combinations thereof.

4. The radial artery signal measuring device of claim 1, wherein the light detector is an organic photodetector.

5. The radial artery signal measuring device of claim 1, wherein the light detector is a quantum dot detector.

* * * * *